(12) United States Patent
Kunz et al.

(10) Patent No.: US 9,937,313 B2
(45) Date of Patent: Apr. 10, 2018

(54) NASAL ADAPTER SYSTEM FOR CPAP RESPIRATION

(71) Applicant: Dräger Medical GmbH, Lübeck (DE)

(72) Inventors: Rainer Kunz, Lübeck (DE); Sandra Böttiger, Lübeck (DE); Stephanie Wagner, Krummesse (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 755 days.

(21) Appl. No.: 14/362,740

(22) PCT Filed: Dec. 3, 2012

(86) PCT No.: PCT/EP2012/004983
§ 371 (c)(1),
(2) Date: Jun. 4, 2014

(87) PCT Pub. No.: WO2013/083258
PCT Pub. Date: Jun. 13, 2013

(65) Prior Publication Data
US 2014/0332005 A1 Nov. 13, 2014

(30) Foreign Application Priority Data
Dec. 5, 2011 (DE) ........................ 10 2011 120 217

(51) Int. Cl.
*A61M 16/06* (2006.01)
*A61M 16/08* (2006.01)
*A61M 16/00* (2006.01)

(52) U.S. Cl.
CPC ...... *A61M 16/065* (2014.02); *A61M 16/0057* (2013.01); *A61M 16/0666* (2013.01);
(Continued)

(58) Field of Classification Search
CPC ............ A61M 16/0057; A61M 16/065; A61M 16/0666; A61M 16/0816; A61M 16/0875;
(Continued)

(56) References Cited

U.S. PATENT DOCUMENTS

| 6,508,249 B2 * | 1/2003 | Hoenig | A61M 16/08 128/202.27 |
| 2004/0112381 A1 * | 6/2004 | Ujhazy | A61M 16/00 128/204.18 |

(Continued)

FOREIGN PATENT DOCUMENTS

| CN | 101772362 A | 7/2010 |
| DE | 202 06 692 U1 | 8/2002 |

(Continued)

*Primary Examiner* — Annette Dixon
(74) *Attorney, Agent, or Firm* — McGlew and Tuttle, P.C.

(57) ABSTRACT

A nose adapter (2) and system, for use in noninvasive respiratory support, has a proximal end, for coupling to the nose, and a distal end for coupling to a ventilation device. An inspiratory channel (6) and an expiratory channel (7) extend between the proximal and distal end. The distal ends of the channels terminate in a respective connection adapter (30, 31) for connecting ventilation tubes (4). The proximal ends of the inspiratory and the expiratory channels are bent inwards 90° such that the openings of the channels face each other. A cylindrical tube element (34), rotatably held between the openings, has a through-opening in the cylindrical circumferential surface of the tube element. A connection nozzle (13) connects to a prong or a nose mask and is formed on the outer face of the rotatable tube element (34), in alignment with the through-opening, such that the connection nozzle can pivot.

23 Claims, 13 Drawing Sheets

(52) U.S. Cl.
CPC .... *A61M 16/0816* (2013.01); *A61M 16/0825* (2014.02); *A61M 16/0833* (2014.02); *A61M 16/0875* (2013.01)

(58) Field of Classification Search
CPC .......... A61M 16/0677; A61M 16/0672; A61M 16/00; A61M 16/0009; A61M 16/0012; A61M 16/0066; A61M 16/0093; A61M 16/06; A61M 16/0616; A61M 16/0622; A61M 16/0633; A61M 16/0644; A61M 16/0655; A61M 16/0683; A61M 16/0694; A61M 16/0825; A61M 16/0833; A61M 16/0883; A61M 16/1055; A61M 16/1065; A61M 16/20; A61M 16/201; A61M 16/202; A61M 16/209; A61M 16/22; A61M 2016/0027; A61M 2016/0039; A61M 2039/242; A61M 2205/0238; A61M 2206/14; A61M 2206/20; A61M 2210/0618; A61M 2230/432; A61M 2240/00; A61M 39/1055
USPC ............ 128/200.24, 200.26, 204.18, 205.11, 128/205.24, 206.11, 206.12, 206.21, 128/206.24, 206.27, 206.28, 207.11, 128/207.13, 207.18
See application file for complete search history.

(56) References Cited

U.S. PATENT DOCUMENTS

| | | |
|---|---|---|
| 2005/0205096 A1* | 9/2005 | Matula, Jr. ........ A61M 16/0666 128/207.11 |
| 2007/0137653 A1 | 6/2007 | Wood |
| 2009/0032018 A1 | 2/2009 | Eaton et al. |
| 2010/0147302 A1 | 6/2010 | Selvarajan et al. |
| 2012/0017901 A1 | 1/2012 | Mainusch et al. |

FOREIGN PATENT DOCUMENTS

| | | | |
|---|---|---|---|
| DE | 20206692 U1 * | 8/2002 | ............ A61M 16/08 |
| DE | 103 29 818 A1 | 1/2005 | |
| DE | 10 2009 016150 A1 | 10/2010 | |
| WO | 03/022341 A1 | 3/2003 | |
| WO | 2008/005578 A2 | 1/2008 | |
| WO | 2011/110961 A1 | 9/2011 | |

\* cited by examiner

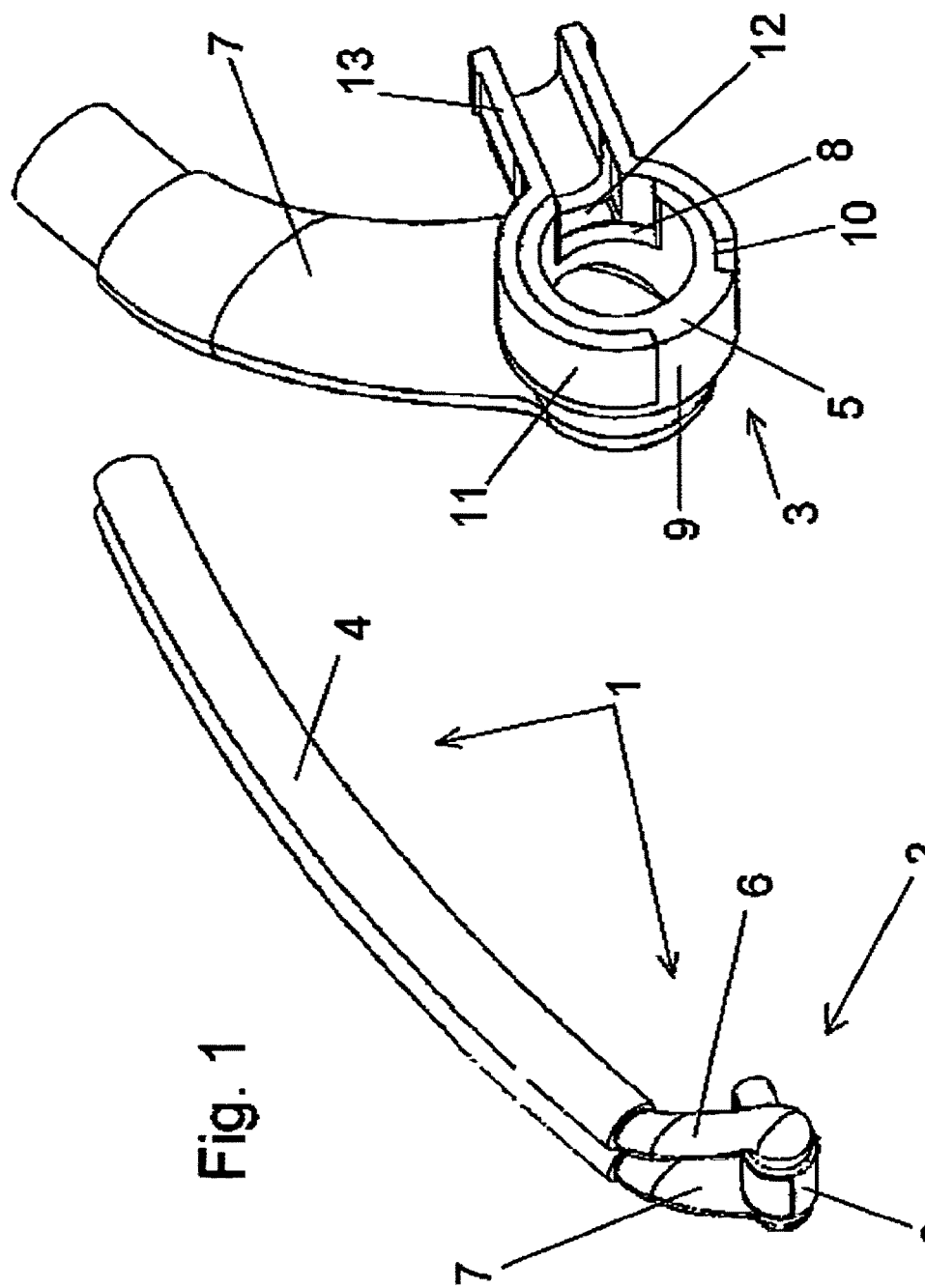

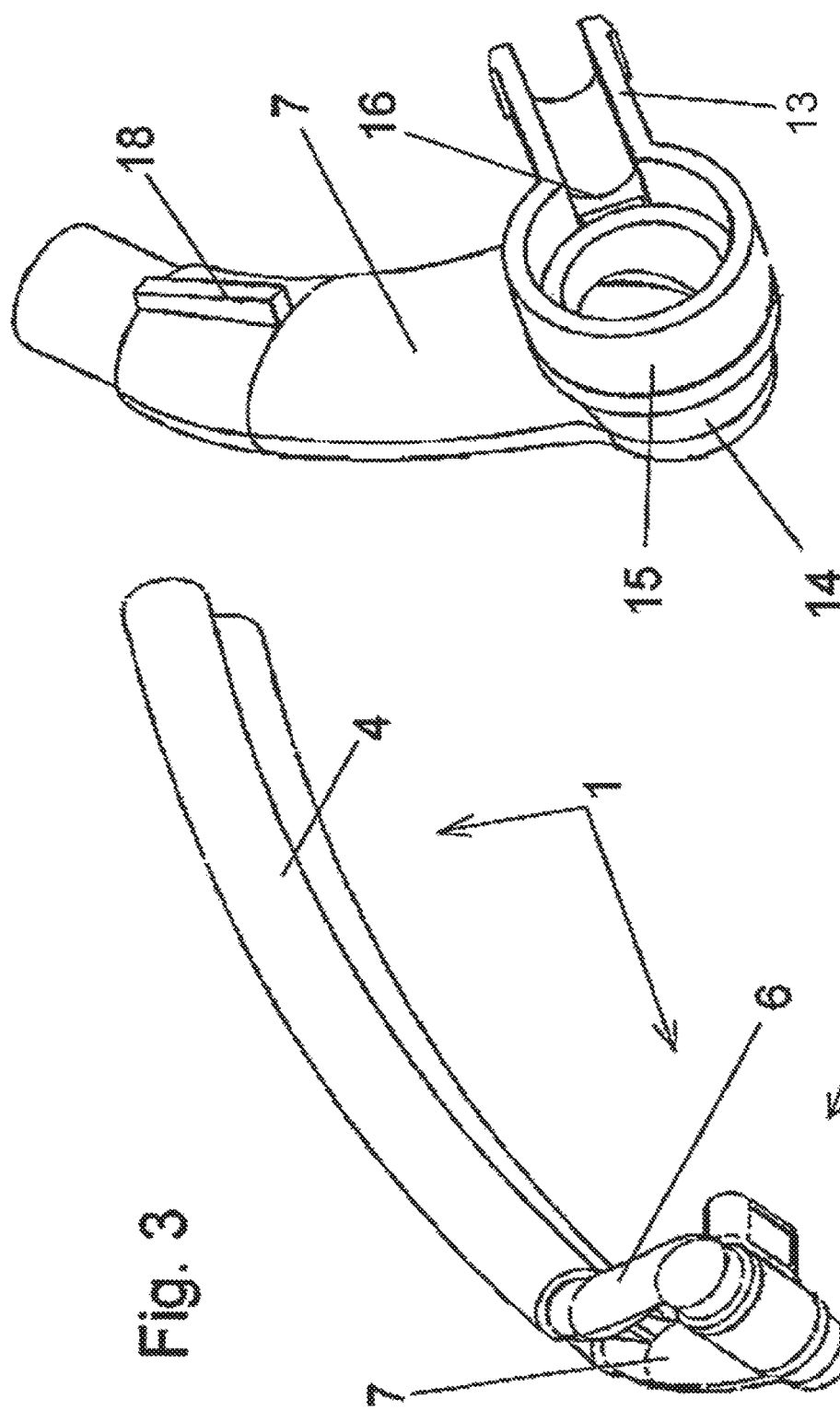

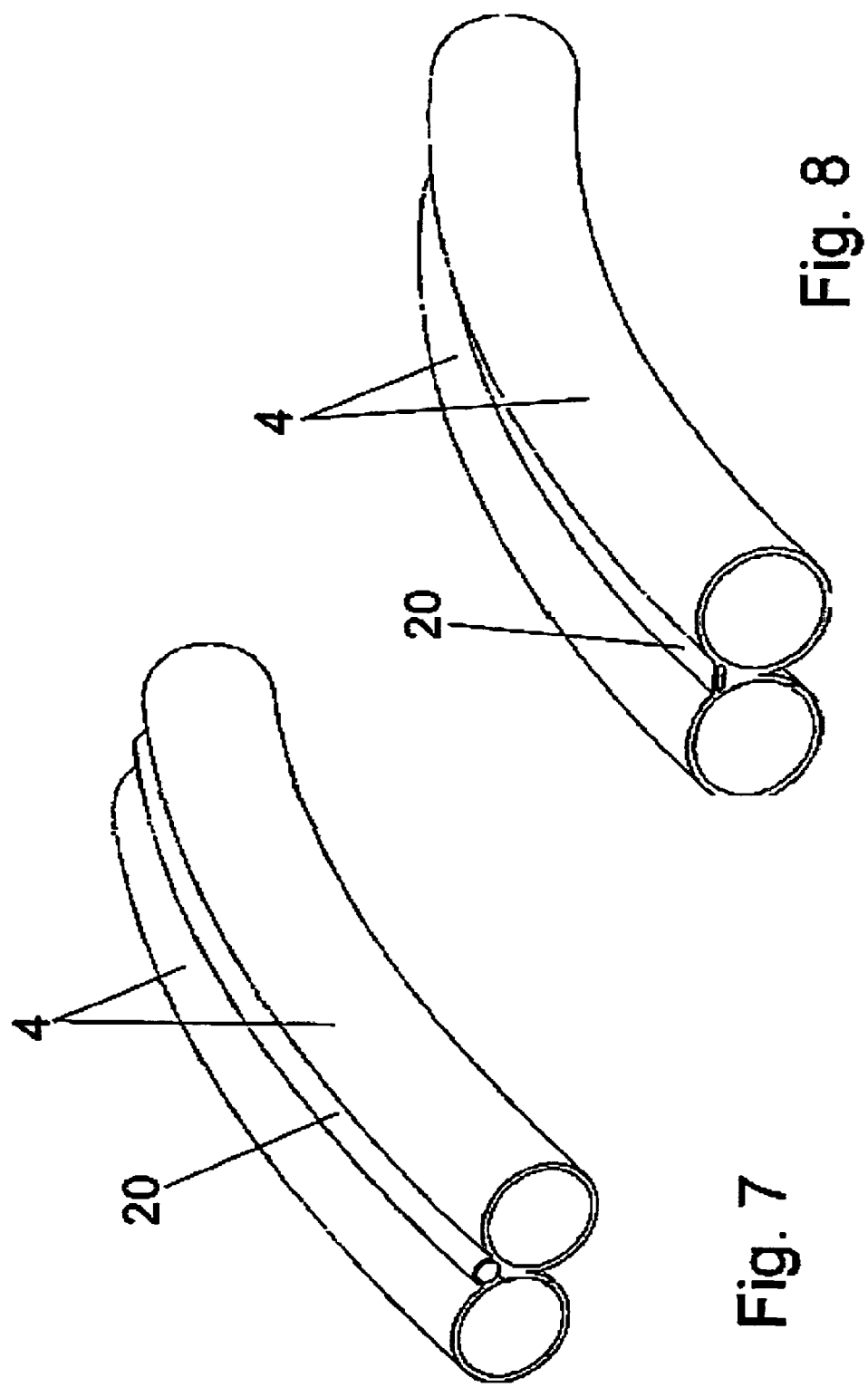

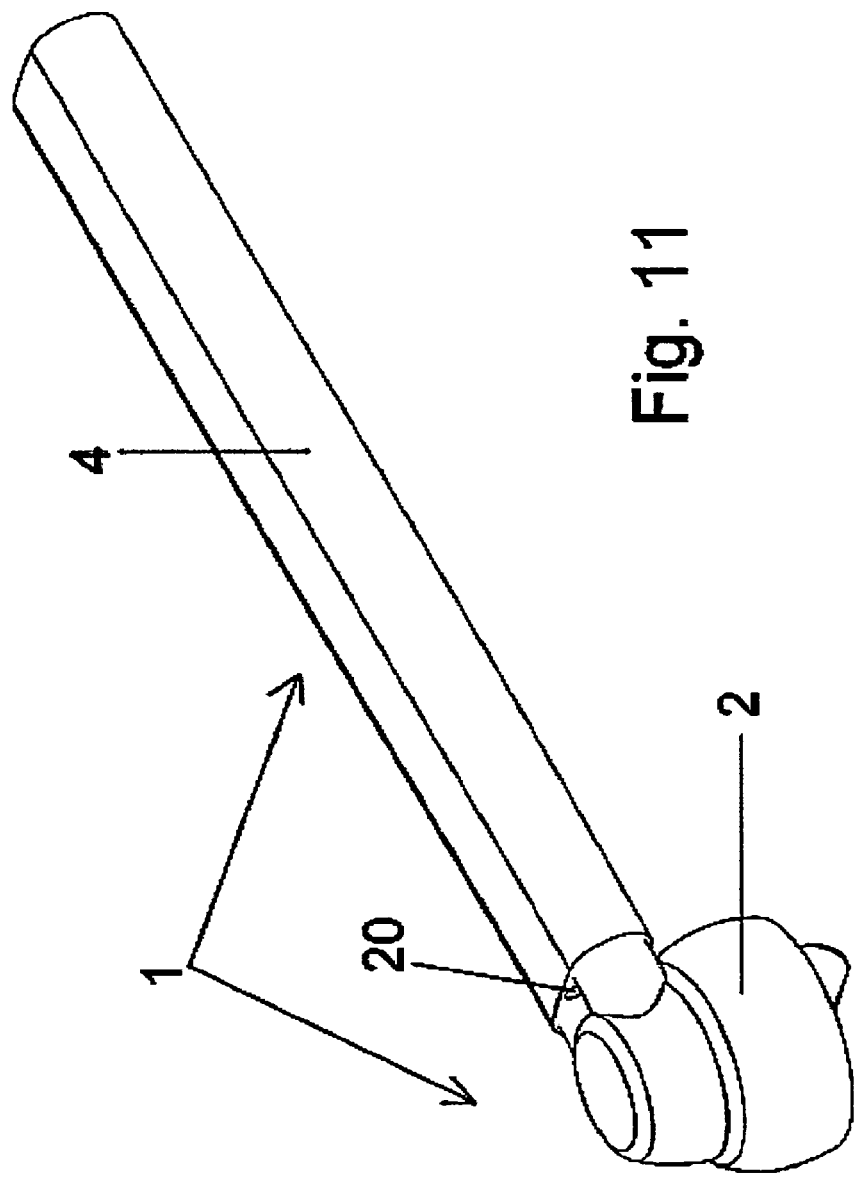

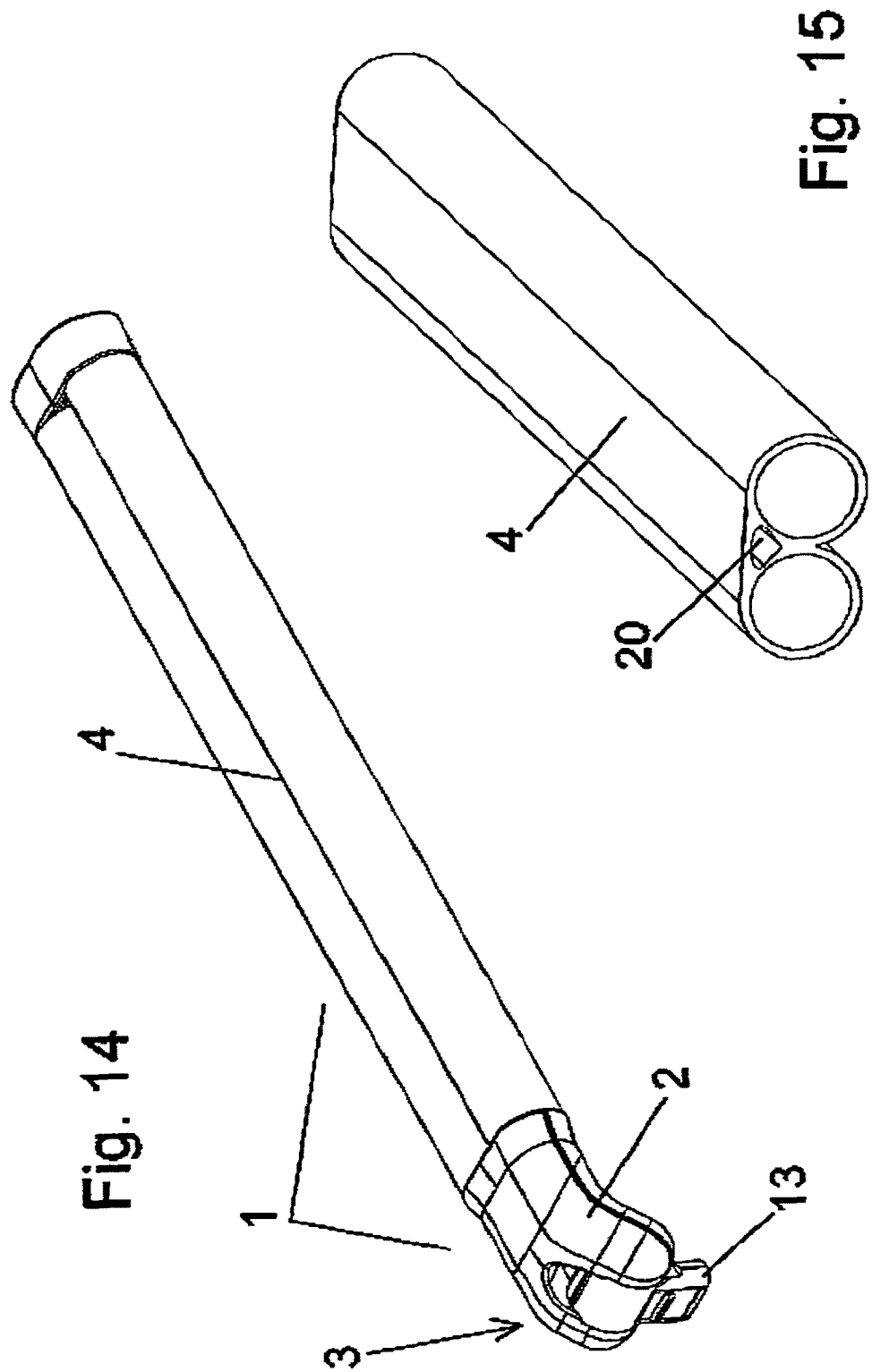

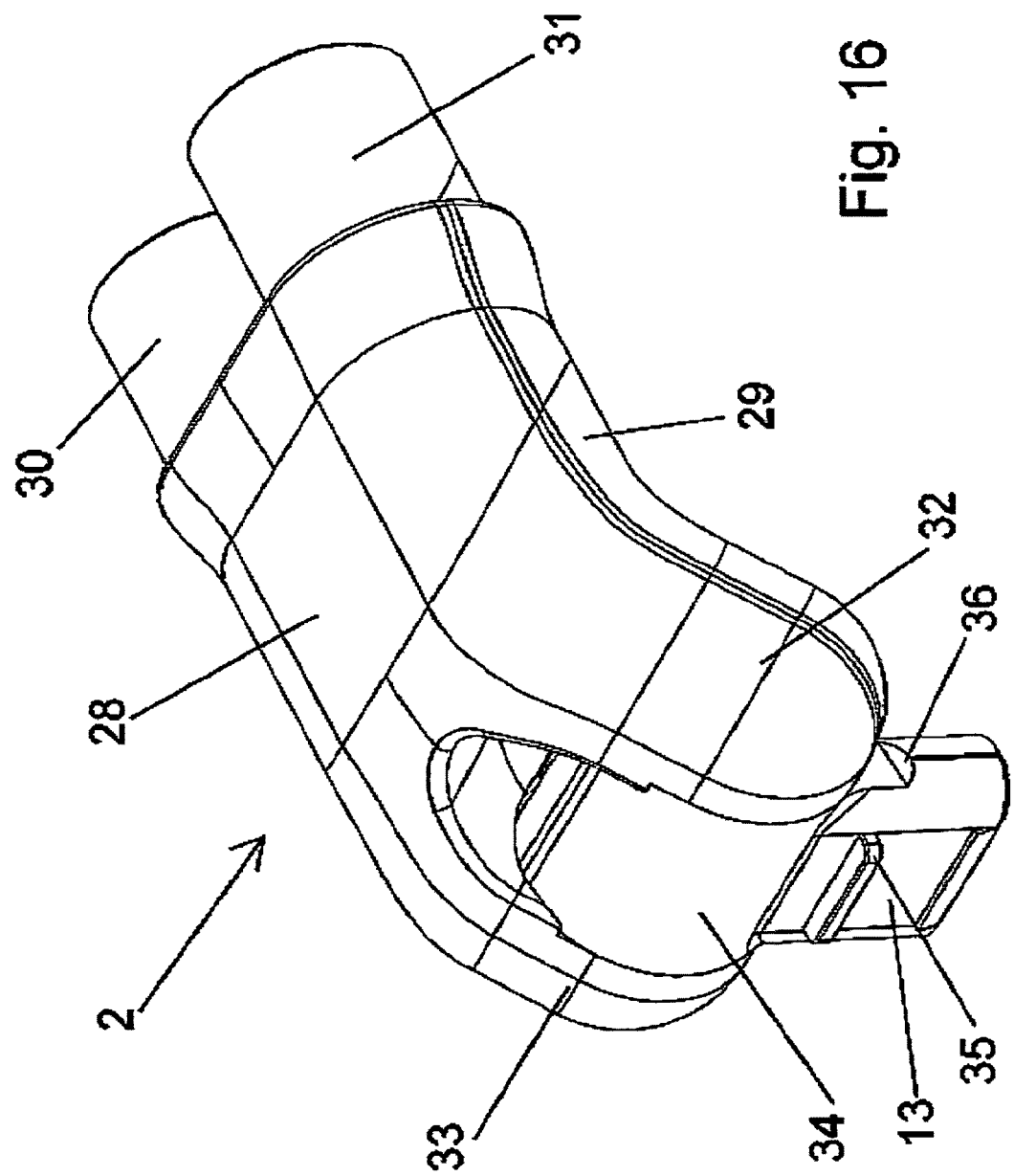

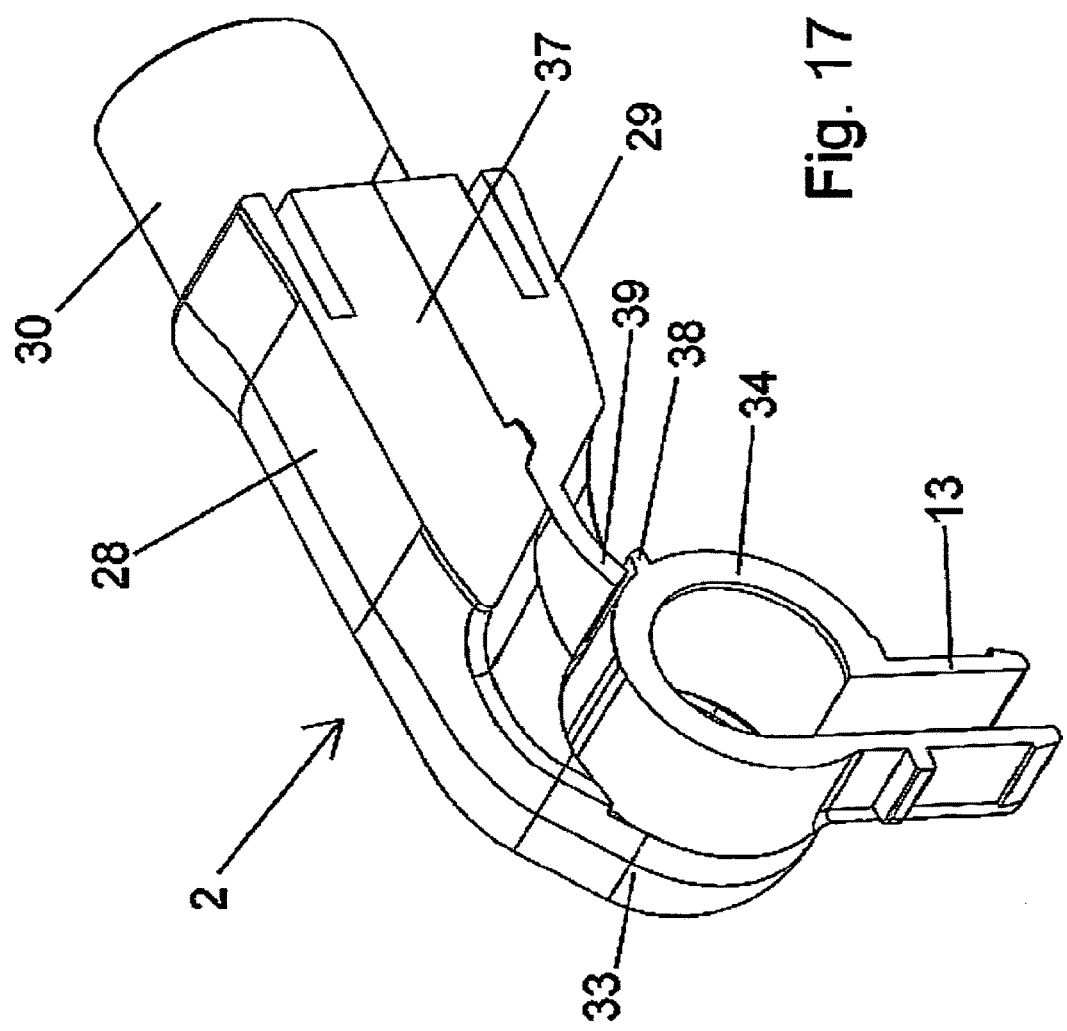

NASAL ADAPTER SYSTEM FOR CPAP RESPIRATION

CROSS REFERENCE TO RELATED APPLICATIONS

This application is a United States National Phase Application of International Application PCT/EP2012/004983 filed Dec. 3, 2012 and claims the benefit of priority under 35 U.S.C. § 119 of German Patent Application DE 10 2011 120 217.3 filed Dec. 5, 2011, the entire contents of which are incorporated herein by reference.

FIELD OF THE INVENTION

The present invention pertains, in general, to a nasal adapter system for use in respiration in the area of intensive care. The present invention pertains, in particular, to a nasal adapter system that is used in CPAP (Continuous Positive Airway Pressure) respiration or NIV-CPAP respiration and is preferably designed to couple a nasal mask or a nasal insert part (hereinafter called "prong") with the breathing tubes (inspiratory tube, expiratory tube and optional auxiliary tubes) of a respirator or other respiration device.

BACKGROUND OF THE INVENTION

There has increasingly been a changeover to non-invasive forms of respiration (NW respiration) in the respiration or respiratory support of newborn and premature infants. The CPAP or NIV-CPAP respiration is one of these forms of respiration. Damage to the upper airways, which may develop due to intubation, shall be avoided by means of NIV respiration. Either nasal masks or prongs or nasal prongs are usually used in NIV respiration.

Nasal masks are usually masks manufactured from silicone rubber, which preferably enclose the patient's nose only and are provided with ports for the breathing tubes. Contrary to this, prongs usually have on their proximal side two small nasal tubes, which are inserted into the patient's two nostrils and have a port for an adapter for connection with the breathing tubes on their distal side. Intermediate tubes (hereinafter called "proximal" tubes), which are coupled at their distal ends with distal breathing tubes, which lead to the respirator or other respiration device, are frequently used in both nasal masks and prongs. The proximal intermediate tubes usually have a smaller cross section than the distal breathing tubes.

Prongs are predominantly used for NW-CPAP respiration. If, however, pressure sores develop on the nose and especially in the nostrils, the prongs may be temporarily replaced with nasal masks, which do not produce pressure sores because of their quality.

The prongs (and also the nasal masks) are attached by laterally arranged, stretchable bands (mostly by means of Velcro fasteners) to a headband or a cap, so that the prong can be held fittingly at the nose and it will not slip off if the patient is moving. The prongs are usually connected to a nasal adapter, which can be coupled at one of its ends to the distal prong port and at its other end to the proximal intermediate tubes. There are prongs of different sizes, depending on the size of the patient, the diameter of and the distance between the nostrils of the patient, into which the nasal tubes of the prong are inserted.

The respiration or respiratory support is usually performed by applying a continuous, positive airway pressure (CPAP). CPAP is a form of respiratory support that requires spontaneous breathing of the patient. Various methods are used to generate the CPAP. The pressure is generated by building up a high-velocity free jet ("jet") in case of the so-called "jet method". Besides, there are methods in which a ventilator feeds a more or less constant volume flow via the inspiratory tube into the breathing system, while an adjustable flow resistance is arranged at the end of the expiratory tube. The pressure develops as a consequence of this flow resistance and the friction in the expiratory tract of the breathing system. The adjustable flow resistance may be generated by a so-called water lock (known as "bubble CPAP") or a regulated expiratory valve.

In all methods mentioned, the inhaled gas must be fed to the patient via tubes. The expired gas must be sent, at least in the method mentioned last, to the ventilator or to the water lock with tubes from the patient. However, the expired gas is usually sent away from the patient in the jet method as well to prevent $CO_2$ from accumulating in the vicinity of the patient.

To keep the volumes and the compliance values of the gas columns as low as possible in the breathing tubes, the tubes of newborn and premature infants, but also of toddlers, are generally smaller than those of adults. For examples, tubes with internal diameters of 11 mm or 15 mm are used in pediatrics and neonatology, whereas tubes for adults practically have an internal diameter of 22 mm without exception.

The connection between the distal tubes (i.e., breathing tubes) and the prong or the nasal mask is usually brought about by so-called CPAP adapter systems (or nasal adapter systems or simply nasal adapters) especially in newborn and premature infants. It shall be mentioned only in passing that such nasal adapter systems may also be used in toddlers or adult patients. However, toddlers and adults frequently breathe through the mouth instead of through the nose, so that face masks are preferably used for respiration for adult patients.

Prior-art nasal adapter systems usually have two proximal tubes with a reduced internal diameter compared to that of the distal breathing tubes and a, for example, Y-shaped adapter headpiece. Various nasal adapter systems are known from the state of the art.

Thus, for example, WO 03/022341 A1 discloses a respiratory support device with a nasal adapter, which is provided with a removable prong, two ports for the breathing tubes and a sensor port. The prong in this nasal adapter has two nasal tubes, which can be inserted into the patient's nostrils. One drawback of the nasal adapter according to WO 03/022341 A1 is that the prong or the nasal tube of the prong can be adapted to different nose sizes (distance and diameter of the nostrils) of different patients only insufficiently at best. Even though the prong and the nasal tubes may be manufactured from a rubber or silicone material, this makes possible only a limited adaptation to different nose shapes (distance and diameter of the nostrils as well as angle of the nostrils relative to the head), so that a large number of different prongs must be kept ready. Great difficulties are caused, in particular, by the adaptation to the angle of the nostrils, because the correct angle of the prong being used can usually be determined only when the complete nasal adapter is placed on the patient's head. It may now happen that the nasal adapter is placed several times on the patient with different prongs until the optimally fitting prong with an optimal angle of the nasal tubes is found. Another drawback of the nasal adapter according to WO 03/022341 A1 is that the air flow is deflected by 180° at the junction between the proximal end of the adapter and the distal end of the prong. The removal of a desired quantity of air from the prong is adversely affected hereby, because the inspired air is pressed with a high impulse into the nasal tubes, as a result of which the patient's expiration is made difficult, which is a drawback especially in newborn and premature infants. Further, the prong has a relatively large dead space due to its design, as a result of which the newborn or premature infant will breathe in again a large portion of the previously expired air during a subsequent breathing cycle. Finally, the breathing tubes of the prior-art nasal adapter are relatively rigid and can be adapted to different head sizes and head shapes of patients with difficulty only.

DE 10 2009 016 150 A1 discloses a nasal adapter or a non-traumatic nasal tube for non-invasive respiratory support, in which the angular position of the entire nasal tube can be changed relative to the forehead support by means of a tilting holder. However, the angle of the nasal adapter or nasal tube relative to the nasal cannula cannot be adjusted. Even though the central tube of the nasal cannula is elastic and is provided with a flexible metal strip to make it possible to adapt the nasal cannula to the shape of the patient's head as best as possible, the degree of freedom obtained hereby is not sufficient for achieving an optimal angular adaptation of the nasal adapter or of the nasal tubes to the patient's nostrils. A further drawback is that corrugated pleated tubes are used in DE 10 2009 016 150 A1, which cannot be adapted continuously, on the one hand, and generate an increased flow resistance compared to a smooth tube due to the pleats present in the interior of the tubes, on the other hand Finally, the pleating of the tubes leads to the possibility of very great variations in the length and hence in the inner volume as well as the compliance of the tube between the original state and the adapted state, on the other hand. This usually has a highly disadvantageous effect on the control characteristics of the ventilator when generating the constant CPAP pressure. Since the nasal adapter has no partition between the inhalation gas and the exhalation gas, the functional dead space is very large.

A bar-shaped, plastically deformable element is arranged between the proximal breathing tubes of a nasal mask device in the solution proposed in DE 103 29 818 A1, and the curvature of these proximal tubes can be permanently changed with this element in order to make it possible to adapt the curvature of the tubes to the size of the head and the shape of the head as a result. The mask device shown in DE 103 29 818 A1 has a nasal mask, whose position relative to the proximal tubes cannot, however, be adjusted, so that the nasal mask can be adapted to the patient's nose only insufficiently. In addition, the breathing tubes must be deformed for reasons of handling (just as in the case of DE 10 2009 016 150 A1) before they are attached to the patient's head. Fine adaptation to the patient's head is difficult because of the forces to be applied for bending the proximal breathing tubes and therefore not practicable. However, precisely this fine adaptation is necessary to prevent the torques applied by the tubes on the nasal mask from leading to one-sided pressure loads in the face or on the nose and hence to possibly irreversible damage to the anatomy of the face.

US 2010/0147302 A1 pertains to a respiration system with a mask system, which has a nozzle assembly unit with two nozzles for connection with the nostrils of a patient. This nozzle assembly unit has a tubular structure and is provided at its opposite ends with two end areas, which can be rotated independently from one another relative to the nozzle assembly unit and are connected to the breathing tubes. The breathing tubes thus extend separately from one another on both sides of the patient's head. It may happen when the patient's head is moving that the nozzle assembly unit becomes detached from the patient's nose.

Finally, DE 202 06 692 U1 discloses, in general, a device for generating a continuous positive airway pressure with an adapter, to which a prong provided with nasal tubes can be attached. However, these nasal tubes are not adjustable, so that no angular adaptation of the nasal tubes to the patient's nostrils can be carried out in this device, either.

The connection between the distal tubes, which are connected with the respirator or other respiration device, and the proximal tubes of the nasal adapter system is usually brought about via conical plug-type connections. However, due to the frictional engagement, such plug-type connections also transmit torques, besides tensile forces and bending torques. This may lead to twisting and, in the worst case, even to occlusion of the proximal tubes of the nasal adapter system when the patient is turning.

As it becomes clear from the above explanations on the state of the art, the drawback of all prior-art nasal adapter systems is that they do not make optimal adaptation of the adapter system to the size and shape of the patient's head possible. In particular, no optimal adaptation of the coupled prongs or of the adapter itself to the nostrils of the patient being respirated can be achieved with the adapter systems according to the state of the art. The nasal adapter may become detached from the patient's nose in the worst case when the patient's head is moved. In addition, the coupling between the adapter and the prong is designed in all prior-art nasal adapters such that the airway resistance is not optimal and a relatively large, so-called dead space becomes established. The latter may lead to the patient rebreathing part of the exhaled air during a subsequent breathing cycle. The $CO_2$ content in the breathing air will increase in this manner continuously during each breathing cycle especially in newborn and premature infants because of the small breathing air volume, because at least part of the air volume enriched with $CO_2$, which remains in the dead space, is inhaled again during each breathing cycle. Finally, the nasal adapter systems according to the state of the art have a complex design, which makes the manufacture of the adapters complicated and expensive.

SUMMARY OF THE INVENTION

A basic object of the present invention is to provide a nasal adapter system or a CPAP nasal adapter system, by means of which the pneumatic connection between the breathing tubes (especially the distal breathing tubes) and a prong or a nasal mask can be designed such that optimal adaptation of the entire nasal adapter system to the shape of the head and the size of the head of the patient to be respirated can be achieved. The adapter system must be able to be adapted to the patient's head, especially to the head of a newborn or premature infant, such that the position of the prong or nasal mask relative to its position in relation to the nose will not possibly change due to movements of the child. Forces and torques that may be generated due to movements of the child and of the breathing tubes relative to one another shall not ideally produce pressure sores on or in the nose or on the face of the child. At the same time, good and simple adaptation to the individual size and shape of the head shall be made possible by the CPAP nasal adapter system according to the present invention. In addition, the CPAP nasal adapter system shall make possible the greatest possible freedom of movement for the child. The flow resistance, especially the expiratory flow resistance, shall also be as low as possible. Finally, the smallest dead space possible shall be obtained due to the nasal adapter system according to the present invention, so that only the smallest possible percentage of the air expired during a preceding breathing cycle will be inhaled again during the current breathing cycle in order to thus minimize the accumulation of $CO_2$ in the patient's airways and/or in the dead space of the adapter system.

According to the invention, a nasal adapter system is provided comprising a nasal adapter, which has patient nose proximal end and a distal end for coupling with a respirator. The nasal adapter comprises an inspiratory channel with an inspiratory channel distal end and an inspiratory channel proximal end having an inspiratory channel opening and an expiratory channel with an expiratory channel distal end and an expiratory channel proximal end having an expiratory channel proximal end opening. A pivot joint is provided with a pivot element pivotably connected to the inspiratory channel at or adjacent to the inspiratory channel proximal end and pivotably connected to the expiratory channel at or adjacent to the expiratory channel proximal end. The pivot joint defines a pivot joint flow passage in fluid communication with the inspiratory channel via the an inspiratory channel opening and in fluid communication with the expiratory channel via the expiratory channel proximal end opening. The pivot element has an outer circumferential surface with a through opening. A connection nozzle extends from the outer circumferential surface of the pivot element. The connection nozzle has a nozzle flow passage in fluid communication with the pivot joint flow passage via the through opening It should be noted that the nasal adapter system according to the present invention is described in this description generally for use in patients who are to be respirated. However, the adapter system is preferably used for newborn and premature infants. The adapter system is preferably used in non-invasive CPAP respiration, but other forms respiration may be theoretically used as well.

To accomplish the above objects, the nasal adapter system according to the present invention must be preferably designed (1) to make possible an angular adjustment of the prongs or nasal mask coupled to (or integrated with) the nasal adapter system relative to the adapter proper, (2) to make it possible to adapt the proximal breathing tubes of the nasal adapter system to the shape and size of the child's head, (3) to offer the greatest possible number of degrees of freedom due to the adapter system in order to limit the freedom of movement of the child to be respirated as little as possible, (4) to keep the dead space of the nasal adapter combined with the prong or the nasal mask as small as possible, and (5) to minimize the flow resistance especially during exhalation.

One or more of the following features are embodied, in principle, by the nasal adapter system according to the present invention:
(1) The CPAP nasal adapter system is provided with a joint, by means of which movement of the nasal adapter in relation to a nasal mask (prong) is made possible in at least one direction.
(2) The breathing tubes (preferably proximal breathing tubes) coupled to the distal end of the adapter are provided with a plastically deformable fiber in order to make it thus possible to adapt the tubes to the shape and the size of the head of the patient, especially a newborn or premature infant. However, the proximal breathing tubes, which are preferably provided between the adapter and the distal breathing tubes, may also be omitted in an alternative embodiment. At least the proximal ends of the breathing tubes may be provided with a plastically deformable fiber in this case.
(3) The proximal breathing tubes of the adapter may be coupled rotatably and/or pivotably to the distal breathing tubes, which are directly or indirectly connected with the respirator.
(4) The nasal adapter and the articulated connection between the adapter and the nasal mask or prong are designed such that they form the smallest dead space possible in order to minimize the accumulation of $CO_2$ within the adapter system and consequently in the airways of the patient.
(5) The breathing gas is routed due to the geometry of the nasal adapter such that a lower flow resistance will develop.

The nasal adapter system according to the present invention for use in non-invasive respiratory support comprises a nasal adapter, which has a proximal end and a distal end, wherein the proximal end is designed for coupling to the nose of a patient to be respirated and the distal end for coupling to a respirator, an inspiratory channel and an expiratory channel, which extend between the proximal end and the distal end of the nasal adapter and are connected to one another, a tube element, which is held rotatably between the proximal ends of the channels and is provided with a through opening in its circumferential surface, and a connection nozzle, which is formed on the outer side of the tube element in alignment with the through opening, wherein the connection nozzle is designed for coupling to the nose of the patient to be respirated.

The nasal adapter system preferably comprises proximal breathing tubes, which are connected at the distal end of the nasal adapter.

The proximal breathing tubes may be connected with one another and coupled to a plastically deformable fiber in the nasal adapter system, wherein the deformable fiber may be a metal wire with a round or rectangular cross section.

The tube element is preferably held between the proximal ends of the channels such as to bring about a fluid connection between the proximal ends of the inspiratory channel and the expiratory channel The distal ends of the inspiratory channel and the expiratory channel are preferably provided with a connection adapter each for connecting a proximal inspiratory tube and a proximal expiratory tube, respectively.

The proximal ends of the inspiratory channel and of the expiratory channel may be bent each inwards at an angle of about 90° such that the proximal openings of the channels face each other.

The adapter may have an upper housing shell and a lower housing shell, which are connected to one another by bonding, welding or by locking means. The inspiratory channel, expiratory channel, and connection adapters, may be formed by the upper housing shell and the lower housing shell here.

Two extensions, between which the tube element is held, may be formed at the proximal end of the adapter. The two extensions are formed on the proximal side of the lower housing shell and the upper housing shell each, and a 90° bend of the inspiratory channel is formed in one extension, and a 90° bend of the expiratory channel is formed in the other extension. Further, the extensions may have an end area, between the flat inner surfaces of which, which face each other, the rotatable tube element is held in connection with the proximal openings of the channels.

The proximal end areas of the inspiratory channel and of the expiratory channel preferably extend in the form of a quarter toroid within the corresponding extensions.

The connection nozzle is in connection with the interior of the tube element in the nasal adapter system according to the present invention, and the two axial end openings of the tube element are in connection with the corresponding proximal openings of the inspiratory channel and of the expiratory channel, respectively.

A projection, which strikes a stop on the adapter housing in an end position, as a result of which excessive rotation of the tube element is prevented, is preferably provided on the tube element.

The connection nozzle may be designed for coupling to a nasal mask or to a prong.

The proximal openings of the inspiratory channel and of the expiratory channel preferably have a circular cross section, which corresponds to the cross section of the cylindrical tube element.

The tube element may be held between the proximal openings of the inspiratory channel and of the expiratory channel such as to make it possible to change the angle set between the nasal adapter and the connection nozzle.

Finally, the proximal breathing tubes and corresponding distal breathing tubes may be connected with one another by a barrel joint, so that each of the proximal breathing tubes is rotatable relative to the corresponding distal breathing tube.

The present invention will be described now on the basis of some exemplary embodiments with reference to the figures, which show different embodiments of the CPAP nasal adapter system according to the present invention. Even though the following description generally pertains to a nasal adapter system, which is used in CPAP respiration or NIV-CPAP respiration, the nasal adapter system according to the present invention may also be designed or used for other applications of respiration and other forms of respiration.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a perspective view showing an exemplary embodiment of the nasal adapter system according to the present invention, in which the proximal breathing tubes are arranged at the distal end of the nasal adapter and wherein the proximal end of the adapter is provided with a cylindrical joint;

FIG. 2 is a cross sectional view of the cylindrical joint from FIG. 1;

FIG. 3 is a perspective view showing an alternative embodiment of the nasal adapter system from FIG. 1, wherein the proximal breathing tubes are arranged at the distal end of the nasal adapter and wherein the proximal end of the adapter is provided with an alternative embodiment of the cylindrical joint used in FIG. 1;

FIG. 4 is a cross sectional view of the cylindrical joint from FIG. 3;

FIG. 7 is a perspective view showing a variant of the solutions shown in FIGS. 5 and 6, in which the breathing tubes are connected to one another, wherein a round metal wire, which is preferably integrated in the material of the breathing tubes, is provided between the two tubes;

FIG. 8 is a perspective view showing a variant of the solution shown in FIG. 7, in which a flat metal wire, which is preferably integrated in the material of the breathing tubes, is provided, instead of the round metal wire, between the two breathing tubes;

FIG. 11 is a perspective view of another embodiment of the nasal adapter system according to the present invention;

FIG. 14 is a perspective view of an alternative embodiment of the nasal adapter system according to the present invention;

FIG. 15 is a perspective view of the proximal breathing tubes from FIG. 14;

FIG. 16 is a perspective view of the nasal adapter from FIG. 14;

FIG. 17 is a cross-sectional view of the adapter from FIG. 16;

DESCRIPTION OF THE PREFERRED EMBODIMENTS

Figure 6:
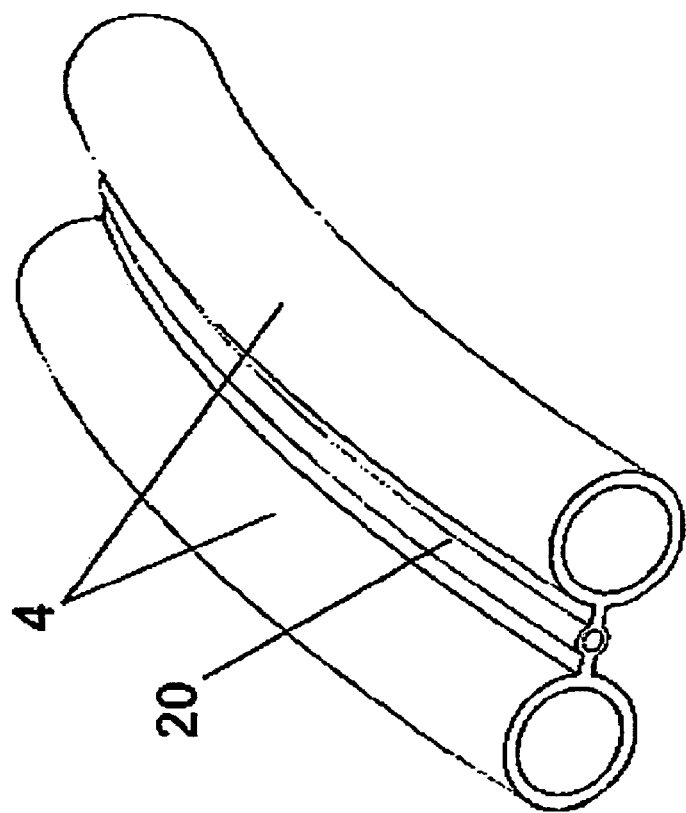
FIG. 6 is a perspective view showing a variant of the solution shown in FIG. 5, in which the three tubes are manufactured or connected in an integrated manner.

Referring to the drawings and in particular with reference to FIG. 1, an exemplary embodiment of the CPAP nasal adapter system 1 according to the present invention will be described below. The nasal adapter system 1 comprises essentially the nasal adapter 2 proper, which is provided with a joint 3 at its proximal end and at the distal end of which the proximal breathing tubes 4 of the adapter system are arranged. Not shown are the distal breathing tubes, which are coupled to the distal ends of the proximal breathing tubes 4 and lead to a respirator (not shown) or to other respiration device. As an alternative, the distal breathing tubes may, however, also be connected directly with the distal end of the adapter 2.

The proximal breathing tubes 4 comprise an inspiratory tube and an expiratory tube, which are arranged next to each other and are connected to one another, as this will be explained below.

As was described above, the proximal ends of the proximal breathing tubes 4 are coupled to distal ports of the adapter 2. The adapter 2 has two inner channels (inspiratory channel 6 and expiratory channel 7), through which the inhaled air and the exhaled air are sent from the breathing tubes to the joint 3 and sent away from said joint 3, respectively. The joint 3 is preferably a cylindrical joint (cylindrical joint), whose middle section, at which a port is provided for a prong or a nasal mask, is rotatable or pivotable relative to the housing proper of the adapter 2 (and hence also relative to the proximal breathing tubes 4). Fine adjustment can be performed due to this rotatable middle section of the cylindrical joint. The swivel joint or cylindrical joint 3 should be smooth running, but it should not move independently under the usual forces that may occur during movements of the newborn or premature infant.

One embodiment of the joint (a pivot joint) 3 from FIG. 1 is shown in FIG. 2, which shows a cross section of this joint. An essentially cylindrical inner tube 5 extends in this joint 3 between the inspiratory channel 6 and the expiratory channel 7 of the adapter 2. As can be seen in FIGS. 1 and 2, this inner tube 5 is mounted between the proximal end sections of the channels 6 and 7 or is made integrally with these. These end sections are preferably essentially hemispherical, so that the air flows from the end section of the inspiratory channel 6 into the inner tube 5 and from the inner tube 5 into the end section of the expiratory channel 7 with a gentle 90° deflection in order to bring about in this manner an air flow with the slightest swirl possible into and out of the inner tube 5. An opening 8, which points essentially in the direction of the patient's nostrils when the adapter system is positioned on the patient's head, is provided in this inner tube 5. The outer surface of this inner tube 5 is provided with a recess or depression 10, which extends almost around the entire circumference of the inner tube 5 and is interrupted by a projection 9 only. As can be seen in FIG. 2, a partially cylindrical slide 11 (part of the pivot joint) is clamped or snapped onto the partially cylindrical recess 10. The slide 11 likewise has an opening 12, which is aligned essentially with the opening 8 of the inner tube 5 or is flush with same. However, the opening 12 of slide 11 has a shorter extension or size in the circumferential direction than does the opening 8 of the cylindrical inner tube 5. The slide 11 being held in or on the recess 10 can be rotated in this manner relative to the inner tube 5. This rotation is limited only by the projection 9. The adjacent sides of the projection 9 and of the slide 11, which sides face each other, are preferably provided with corresponding undercuts, so that the slide 11 cannot be pushed accidentally over the projection 9, because the undercuts mesh with one another. The limitation of the rotation of slide 11 by the projection 9 prevents the openings 8, 12 from being able to become mutually closed. The opening 12 of the slide consequently always remains essentially in alignment with the opening 8 of the inner tube 5 during the rotation of the slide 11, and the opening cross section of the openings 8 and 12 becoming superimposed to one another remains constant regardless of the angle of rotation of the slide 11 relative to the inner tube 5, because the opening 8 of the inner tube 5 extends over a greater length in the circumferential direction of the inner tube 5 than does the opening 12 of the slide 11. The cross section of the superimposed openings 8 and 12 is consequently defined by the smaller cross section of the opening 12 of the slide 11. As an alternative, the opening 12 of the slide 11 may, however, also have a greater extension than the opening 8 of the inner tube 5, as a result of which the same effect is achieved. In agreement with the opening 12, a connection nozzle 13 is provided on the outer side of the slide 11, and this connection nozzle 13 is used to become coupled to a nasal mask or to a prong.

As can be seen in FIGS. 1 and 2, the distal ends of the inspiratory channel 6 and expiratory channel 7 of the adapter 2 are coupled to the proximal breathing tubes via the extended connection tubes or connection adapters of these channels or alternatively directly to the distal breathing tubes. The gas flow of the respirator consequently leads from the proximal inspiratory tube into the inspiratory channel 6 of the adapter 2, flows through the cylindrical inner tube 5 past the openings 8 and 12 (windows displaceable in relation to one another), and escapes through the expiratory channel 7 of the nasal adapter 2 and through the proximal expiratory tube back to the respirator. The patient can take a needed quantity of the air flowing through the inner tube 5 via the connection nozzle 13 during inhalation and feed it back during exhalation. The path of gas between the inner tube 5 and the nozzle 13 is prevented by the projection 9, which forms a kind of a means securing against rotation, from becoming closed by an excessively great pivoting motion of the slide 11.

The patient to be respirated, who wears the prong (whose nasal tubes are inserted into the patient's nostrils and who is coupled to the connection nozzle 13 of the slide 11), takes the needed quantity of air during each breathing cycle from the air flowing through the inner tube 5 through the connection nozzle 13 and through the openings 8, 12 and releases the exhaled air back again into the adapter 2 (i.e., into the inner tube 5), and the exhaled air is entrained by the air flow flowing through the inner tube 5. The flow curves within the adapter 2 will be discussed in detail later.

Even though the inspiratory channel 6 and the expiratory channel 7 are shown as separate channels in FIGS. 1 and 2, the channels 6, 7 may also be connected with one another or made integrally with one another (preferably along their longitudinal direction). As is indicated in FIG. 1, the channels 6, 7 may be formed in the form of a "Y" with one another.

In another exemplary embodiment, which is shown in FIGS. 3 and 4, the nasal adapter 2 of the nasal adapter system 1 has essentially the same design as in FIGS. 1 and 2. As can be seen in FIG. 4, the proximal ends of the inspiratory channel 6 and of the expiratory channel 7 are provided with a connection part 14 each, which has a circular connection opening each, i.e., the inspiratory channel 6 terminates with a connection part 14, from which the inhalation air is discharged, and the expiratory channel 7 terminates with an opposite connection part 14, into which air enters. A tube element 15 (part of a pivot joint), which is coupled rotatably to the two connection parts 14, is located between the two connection parts 14. The two connection parts 14 are essentially hemispherical in this case as well in order to bring about a gentle 90° deflection of the air into and out of the tube element 15. Further, the tube element 15 is provided with an opening 16 and is provided on its outer surface with a connection nozzle 13, which is aligned with the opening 16. Just as in the previous exemplary embodiment, the connection nozzle 13 can be connected to a corresponding port of a prong or of as nasal mask. It is possible in both exemplary embodiments to replace the connection nozzle, which can be seen best in FIGS. 2 and 4, with two nasal tubes, which can be inserted directly (i.e., without the use of a prong) into the patient's nostrils.

It can be seen in FIGS. 2 and 4 that the axis of the respective connection nozzle 13 intersects the axis of the inner tube 5 or of the tube element 15. However, the connection nozzle 13 will preferably extend tangentially to the inner tube 5 (or to the tube element 15), as a result of which the flow characteristics are improved.

No means for securing against rotation (see projection 9 in FIG. 2) is necessary in the exemplary embodiment shown in FIGS. 3 and 4. The rotationally symmetrical shape of the parting or coupling surface between the circular openings of the connection parts 14 and the corresponding, likewise circular openings of the tube element 15 facilitates the sealing function in this case. The two extended nozzles or tubings of the inspiratory channel 6 and of the expiratory channel 7 are held together by a connection element 18, which is formed, for example, by a web and a corresponding groove element, which mesh with one another, as a result of which the cylindrical tube element 15 is clamped between the expiratory channel 7 and the inspiratory channel 6 (or between the connection parts 14). As an alternative, the expiratory channel 7 and the inspiratory channel 6 may be connected by a connection element 18 formed integrally with these channels. A spring force, by which the tube element 15 is held clamped between the connection parts 14 of the channels 6 and 7, is generated now by the connection element 18. The channels may also be connected permanently to one another or integrated with one another in the area of the connection element 18 shown in FIG. 4 in another embodiment. The adapter has essentially the shape of a "Y" in this case as well, as is apparent from FIG. 3. The adapter (with the exception of the tube element 15) may be manufactured in one piece due to this design. As a consequence, the channels 6, 7 extend (just as in the embodiment according to FIGS. 1 and 2) essentially in parallel to one another. Further, the distal ends or connections for connecting the breathing tubes are arranged next to each other, as a result of which the connection of the breathing tubes, which are designed as "twin tubes" (preferably in an integrated form) and thus extend in parallel to one another, is facilitated. The channels 6, 7 of the adapter and the breathing tubes connected thereto extend in this manner essentially in parallel to one another.

As was stated in the introduction, the object of the present invention is, among other things, to provide a nasal adapter system, by means of which the greatest possible number of freedoms are achieved. An essential degree of freedom is achieved by the cylindrical joint (which is also called barrel joint) in the adapter housing itself, as a result of which the connection nozzle, which is connected with the prong or the nasal mask, can be rotated freely in relation to the nasal adapter or the channels 6 and 7, as a result of which the prong or the nasal mask can, in turn, be optimally adapted to the patient's nose.

A further degree of freedom is achieved by providing a rotatable coupling between the proximal breathing tubes 4 and the corresponding inspiratory channel 6 or expiratory channel 7 of the nasal adapter. The proximal inspiratory tube can be rotated in this manner relative to its corresponding inspiratory channel 6, and the proximal expiratory tube can be rotated relative to its corresponding expiratory channel 7.

To make possible the rotation of the proximal breathing tubes 4 relative to the distal breathing tubes, the coupling between these tubes is likewise designed as a rotatable coupling. Such a coupling is shown, for example, in FIG. 10 and will be described in detail below. The patient can move to a greater extent without excessive forces being applied to the nasal adapter system according to the present invention due to these degrees of freedom in rotation. The transmission of axial rotations of the distal tubes to the nasal adapter system is essentially prevented from occurring especially by the rotatable couplings between the proximal tubes and the distal tubes. Consequently, movements of the patients are extensively prevented from leading to undesired forces and torques on the nasal mask or the prong.

Figure 5:
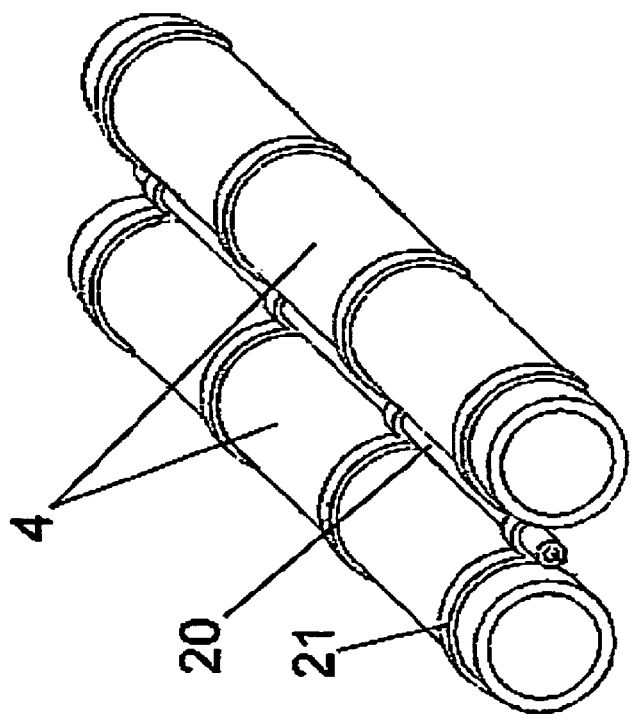
FIG. 5 is a perspective view showing the proximal tubes (i.e., the expiratory tube and the inspiratory tube) of the adapter system according to the present invention, between which a third tube is provided, wherein all three tubes are fastened to one another by clamps.

An exemplary embodiment of the proximal breathing tubes 4 according to the present invention will be described below with reference to FIG. 5. As can be seen, the proximal breathing tubes 4 are connected via a plastically deformable fiber 20, which is located between the two tubes. A total of three tubes, namely, two breathing tubes and a third tube, located between them, in which the fiber 20 is accommodated, are provided in this exemplary embodiment. Thus, all three tubes extend in parallel to one another. It is, of course, also possible to arrange the fiber 20 directly (i.e., without the third tube) between the breathing tubes. The connection of all three tubes may be achieved, for example, by external elements (for example, holding clamps 21) or by the three tubes being manufactured in an integrated form with one another, as this is shown in FIG. 6. For example, an extrusion method may be used for this. However, the three tubes could also be manufactured one by one and then welded or bonded to one another. It is obvious that the plastically deformable fiber 20, for example, a round metal wire or a flattened metal wire, is led in a positive-locking manner in the third intermediate tube. Deformation of the entire proximal tube and hence improved adaptation of the nasal adapter system to the patient's head can be achieved by the plastic deformation of the fiber. A flattened metal wire (i.e., a metal wire with an essentially rectangular cross section) is preferred because a round metal wire may easily twist during bending. It is obvious that the wire 20 may also consist of another material instead of metal.

This possibility of coarse adaptation is especially suitable for preadaptation to size conditions as they correspond, for example, to the size of a child's head. This adaptation may take place before the adapter is attached to the child's head. A finer adaptation of the nasal mask or of the prong to the geometry of the nose, e.g., the angle between the septum and the face, is preferably performed only when the adapter is already attached to the child's head. A fine adjustment by means of a plastically deformable fiber would now be unsuitable, because a fine adjustment of the angle by a few degrees on the child's head is not practicable against the force that is necessary to bend the fiber. Attempts to nevertheless bend the fiber with the adapter in place may cause damage to the skin at the contact sites.

FIGS. 7 and 8 show further embodiments of the proximal breathing tubes with a plastically deformable fiber 20. The fiber 20 is located in FIG. 7 at the connection point between the two breathing tubes extending in parallel to one another and it has a circular cross section. The fiber is likewise located at the connection point between the two tubes in FIG. 8, but it has an essentially rectangular cross section and is embedded in the material of the tube. However, the fiber may also have another cross section, for example, a round cross section, in the exemplary embodiment shown in FIG. 8.

Figure 9B:
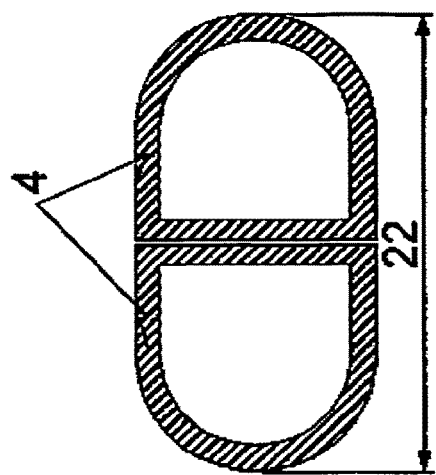
FIG. 9b is a cross sectional view of a second embodiment of the proximal breathing tubes connected in pairs, wherein non-circular sections are used in the second embodiment.
Figure 9A:
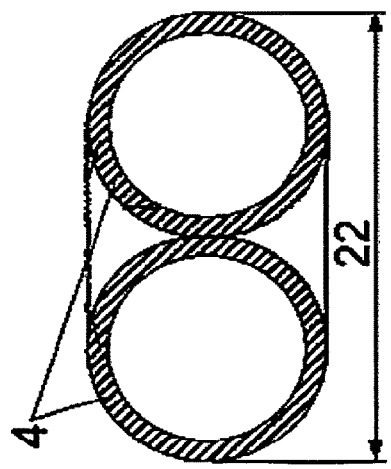
FIG. 9a is a cross sectional view of a first embodiment of the proximal breathing tubes connected in pairs, wherein circular sections are used in the first embodiment.

The proximal breathing tubes 4 usually have a circular cross section (as is shown in FIG. 9*a*) because such tubes can be manufactured (preferably in one piece and in an integrated form) in a simple manner and at low cost in large quantities. If such tubes are to be routed close and in parallel to one another, there will be a certain lateral extension 22 in case of a preset tube diameter. If this extension is to be kept as small as possible, because, for example, the tubes are disturbing over the bridge of the child's nose and may lead to squinting of the child, the diameter of the tubes must be reduced in case of circular cross section of the tubes. A reduction of the cross section leads to a reduction of the cross-sectional area, which is available for the flow, and thus it leads to an increase in the flow resistance. Non-circular sections can be used if the cross-sectional area is to be enlarged in case of a given lateral extension 22. Such sections may consist, for example, of a segment of a circle or ellipse and a rectangle (see FIG. 9b), and the two rectangular areas of the tube cross sections of the inspiratory tube and expiratory tube are preferably arranged in parallel next to each other and are preferably integrated with one another. The plastically deformable fiber may be embedded in the material of the tubes at the connection point between the two tubes in the case of FIG. 9b.

Figure 10:
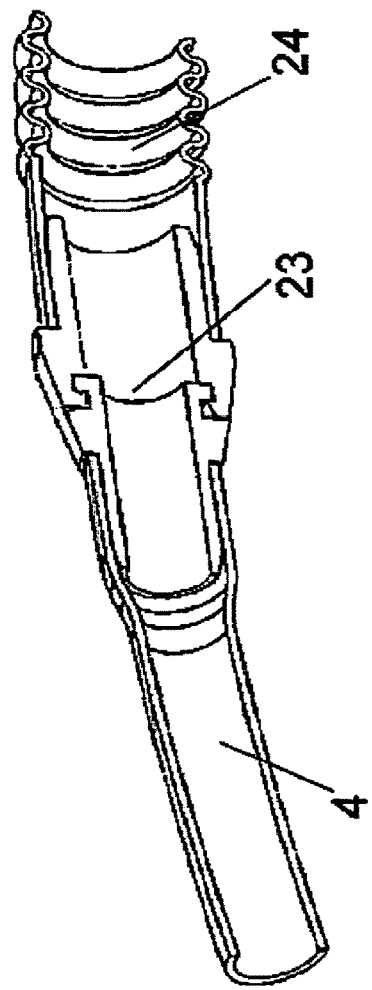
FIG. 10 is a cross sectional view of a barrel joint, by means of which each of the proximal breathing tubes is connected with a corresponding distal breathing tube.

FIG. 10 shows an example of a rotatable coupling 23 between a proximal breathing tube 4 and a distal breathing tube 24 based on the example of a simple locking connection, in which a circular, ring-shaped collar on the end piece of the proximal breathing tube 4 rotatably meshes with a correspondingly shaped groove in the end piece of the distal breathing tube 24. However, many other technical possibilities are known to the person skilled in the art for achieving such a rotatable coupling.

FIG. 11 shows another embodiment of the nasal adapter system 1 according to the present invention. The proximal breathing tubes 4 are coupled with the nasal adapter 2 in this case as well, and the plastically deformable fiber is embedded in the material of the tube between the two breathing tubes such that the pair of tubes has a flat surface at least on the upper side. The design of the adapter 2 will be discussed below.

Figure 12B:
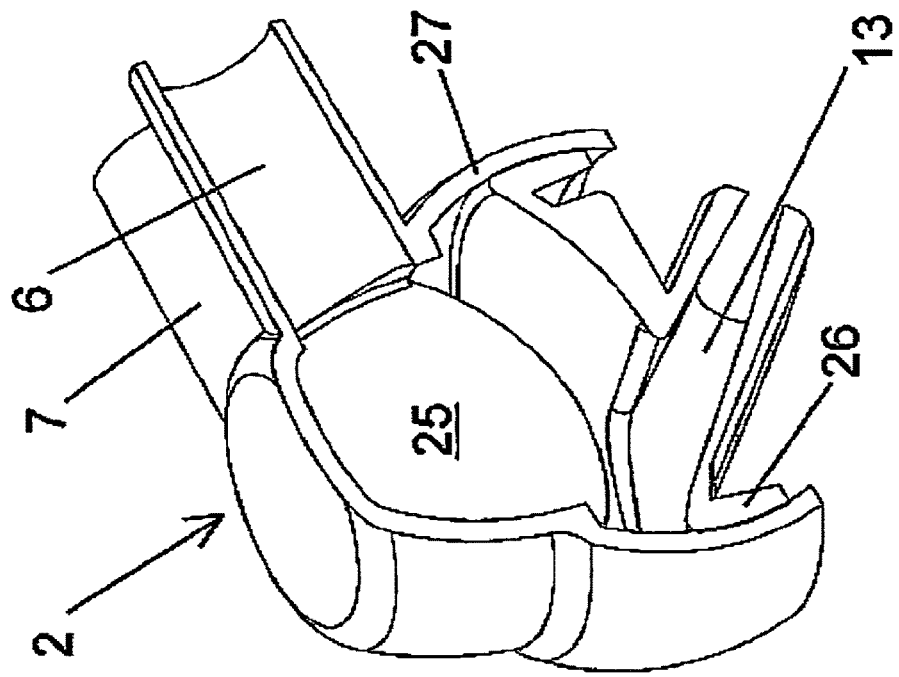
FIG. 12b is a cross sectional view of the joint from FIG. 12a in another sectional plane.
Figure 12A:
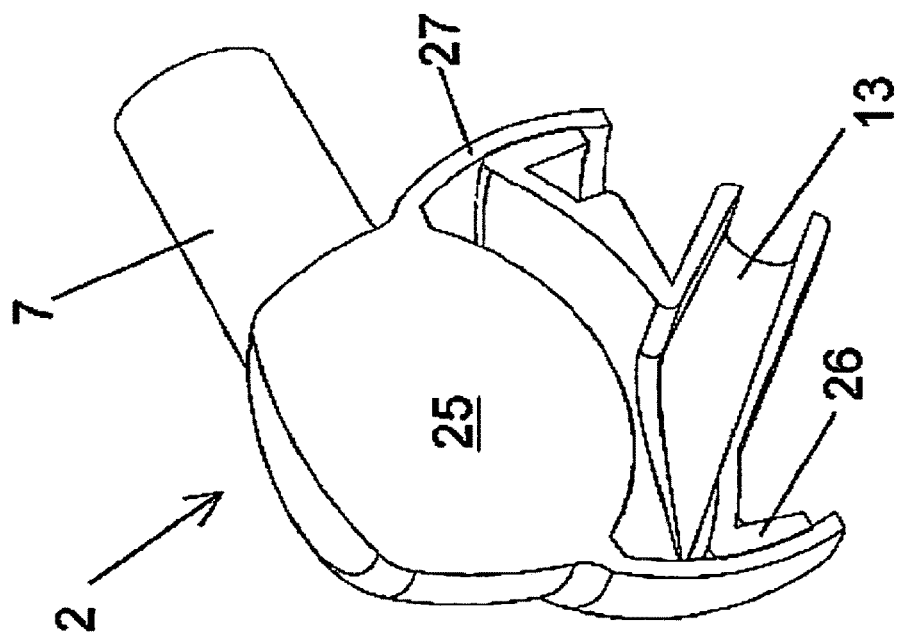
FIG. 12a is a cross sectional view of an embodiment of the adapter joint of the adapter system from FIG. 11.

FIGS. 12a and 12b show the adapter 2 from FIG. 11 in different sectional planes. FIG. 12a shows an essentially central sectional plane, whereas FIG. 12b shows a sectional plane offset slightly in the forward direction. Only the expiratory channel 7 is shown in FIG. 12a, while the inspiratory channel 6 is additionally shown in a sectional view in FIG. 12b. It can be clearly seen in FIG. 12a that a partition 25, by which the inspiratory channel and the expiratory channel are extended up into the proximal part of the adapter housing, in order to reduce the dead space in this manner, extends in the interior of the adapter. If the partition 25 were not present, the dead space would extend over the entire interior space of the adapter 2, which would lead to an undesired accumulation of $CO_2$ in the interior of the adapter. It also becomes clear from FIGS. 12a, 12b that the channels 6, 7 extend next to each other and in parallel to one another. The channels 6, 7 are preferably formed such that they are integrated with one another, as is apparent from FIG. 12b.

The connection nozzle 13, which is connected with a prong or a nasal mask, is formed integrated with a spherical segment 26, which is dimensioned to be able to be rotated and pivoted in all directions in a correspondingly shaped and dimensioned "ball socket" 27 (segment 26 and socket 27 are parts of a pivot joint). A joint with maximum freedom of movement in respect to the alignment of the connection nozzle 13 is obtained in this manner.

Figure 13B:
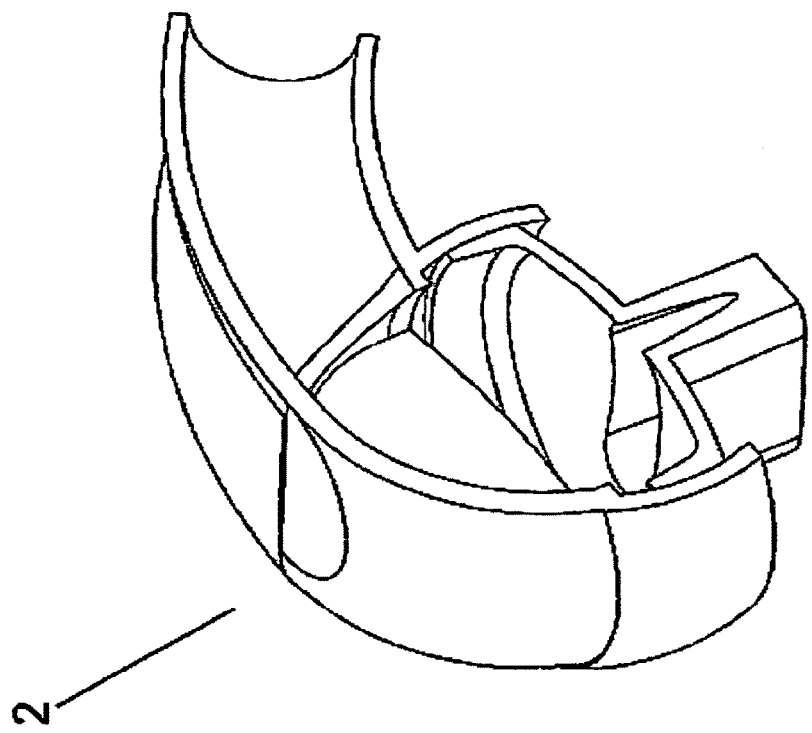
FIG. 13b is a cross sectional view of the adapter joint from FIG. 13a in another sectional plane.
Figure 13A:
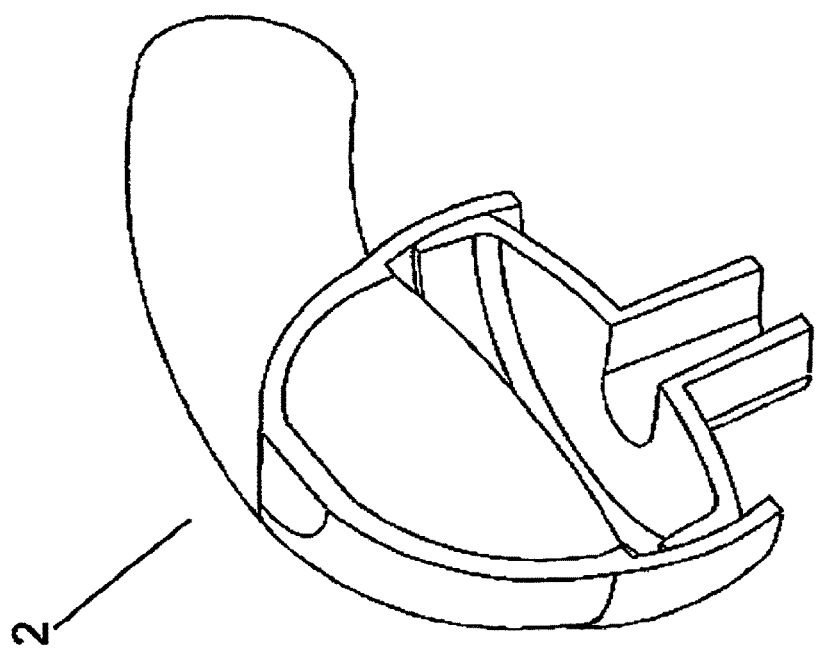
FIG. 13a is a cross sectional view of a variant of the adapter joint from FIGS. 12a and 12b.

FIGS. 13a and 13b show a variant of the adapter shown in FIGS. 12a and 12b. The housing of the adapter 2 according to FIGS. 13a and 13b has an essentially hemispherical shape, as a result of which the flow characteristics of the air flowing into the adapter and flowing out of the adapter are improved. The channels may be arranged in parallel next to each other and may be preferably formed integrated with one another in this case as well. The pivot joint is essentially similar to that of FIGS. 12a and 12b.

FIG. 14 shows another embodiment of the nasal adapter system 1 according to the present invention, and FIG. 15 shows a view of the proximal breathing tubes 4 with an inserted channel for receiving a plastically deformable fiber 20. The joint 3 shown in FIG. 14 for movably aligning the connection nozzle 13 will be described in more detail below with reference to the following figures.

FIG. 16 shows an enlarged perspective view of the adapter 2 from FIG. 14. The housing of this adapter has essentially an upper housing shell 28 and a lower housing shell 29, which are connected to one another by bonding, welding or by locking means. Connection tubes, which are arranged next to each other and in parallel to one another, are formed at the distal end of the adapter, the tube 31 being connected with the proximal inspiratory tube and the tube 30 being connected with the proximal expiratory tube. Based on the parallel arrangement of the tubes 30, 31, the tubes may also be arranged in parallel to one another and preferably connected to one another, as was already explained above. In view of the embodiments according to FIGS. 1 through 4, it is obvious that tube 31 (or the connection adapter) is connected with the inspiratory channel of the adapter, and that tube 30 is connected with the expiratory channel of the adapter, and the two channels extend in parallel next to each other and are separated from each other by a partition (not shown). The tubes 30, 31 (just like the channels) may be formed integrated with the lower housing shell 29 and/or with the upper housing shell 28. Two extensions 32, 33 are formed on the proximal side of the adapter housing, so that the adapter housing is essentially Y-shaped. The inspiratory channel is continued in the extension 32, and the expiratory channel is continued in the extension 33. Both extensions 32, 33 have an essentially spherical quadrant-shaped end area, in the flat lateral surfaces of which, which face each other, circular openings are formed, between which a rotatable tube element (part of a pivot element) 34 is held, at which the connection nozzle 13 is formed. It is apparent from FIG. 16, the axis of the tube element 34 coincides with the centers of the two openings formed in the extensions 32, 33, so that the tube element 34 can be rotated about its axis, wherein the connection between the circular ends of the cylindrical tube element 34 and the circular openings of the extensions 32 and 33 is essentially air-tight. As was mentioned, the connection nozzle 13 is in connection with the interior of the tube element 34, and the two axial end openings of the tube element are in connection with corresponding openings in the two extensions 32, 33. A flow path is thus obtained from the tube 31 (or the connection adapter) through the inspiratory channel of the adapter, through the tube element 34, through the expiratory channel of the adapter to the tube 30 (or the connection adapter). The air flow in the tube element 34 now flows past the opening in the wall of the tube element, at which the connection nozzle 13 is formed. The extensions 32 and 33 are sloped slightly downward relative to the adapter housing, as can be seen in FIG. 16, in order to make possible an expanded angle of rotation. In addition, a projection 35, which acts as a stop for the prong or the nasal mask, is formed at the connection nozzle 13. Another projection 36 on each narrow side of the nozzle is used to improve the holding of the prong or mask at the nozzle.

FIG. 17 shows a cross-sectional view of the adapter 2 from FIG. 16. The upper housing shell 28, the lower housing shell 29 and the partition 37, by which the inspiratory channel is separated from the expiatory channel extending in parallel, can be seen. Further, it can be recognized that the laterally inwardly pointing opening in the extension 33 of the expiratory channel is open towards the corresponding axial end opening of the tube element 34. Another projection 38, by which the tube element is prevented from being rotated excessively rearwardly when the projection 38 strikes a stop 39 on the lower housing shell of the adapter housing 2, is provided on the rear outer side of the tube element 34.

Figure 18B:
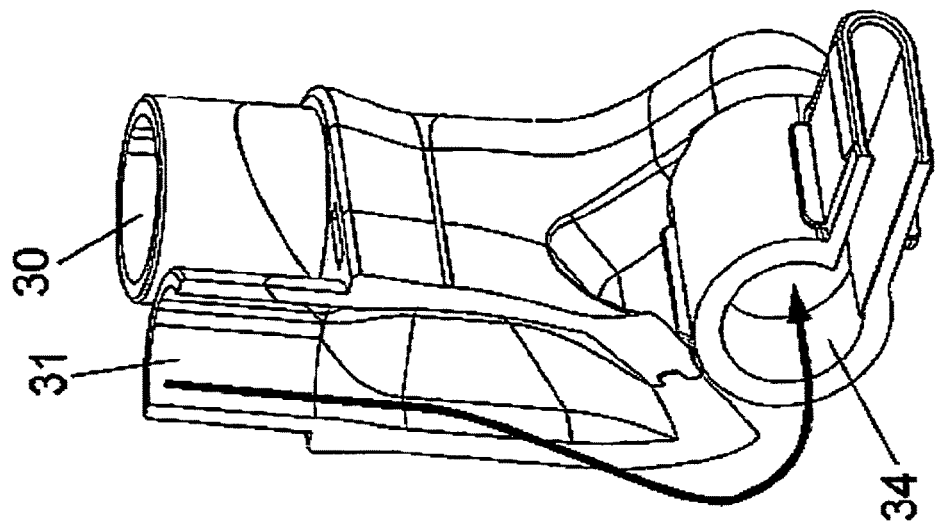
FIG. 18b is a cross sectional view showing a course of flow of air used for respiration through the adapter from FIGS. 16 and 17.
Figure 18A:
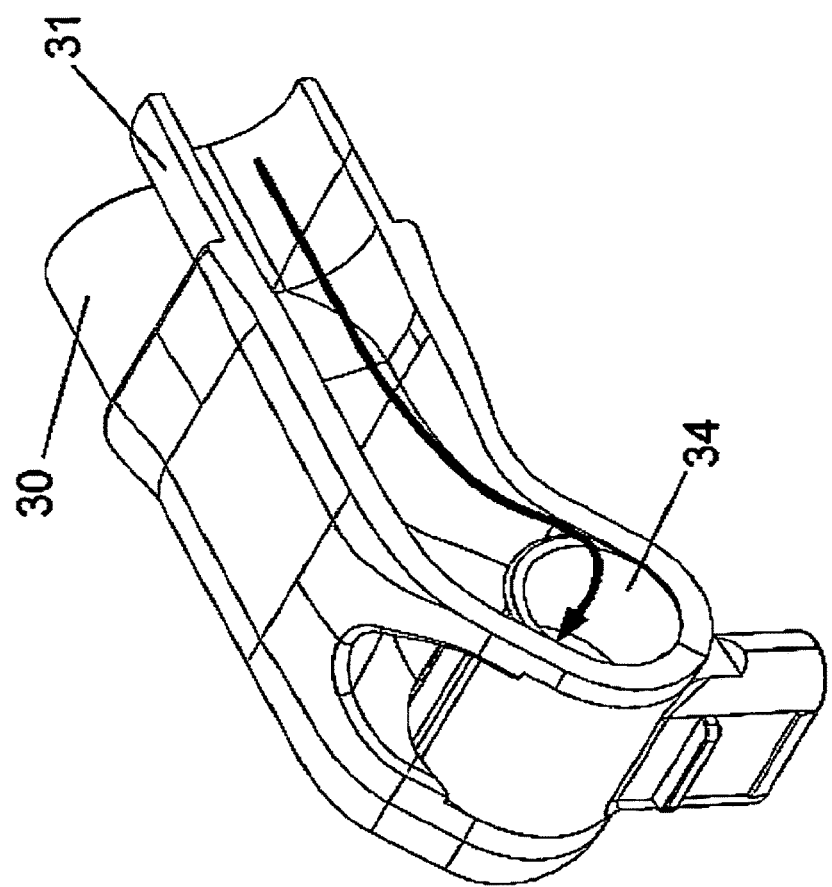
FIG. 18a is a cross sectional view showing a course of flow of air used for respiration through the adapter from FIGS. 16 and 17.

FIGS. 18a and 18b show further cross-sectional views of the adapter 2 from FIGS. 16 and 17 in different sectional planes. The course of the flow of the air flowing through the tube 31 into the inspiratory channel is also shown in these views. As can be clearly seen, the air flows with a gentle 90° bend from the inspiratory channel into the tube element 34, which is due to the fact that the extensions shown in FIGS. 16 and 17 have the shape of a spherical quadrant. Based on this low-swirl inflow into the tube element 34, intense swirling is also avoided in the interior of the tube element. The so-called WOB (work of breathing) is thus kept low. Further, it is achieved that the dead space has an extremely small volume. In addition, it can be seen that a compact design of the adapter can be obtained due to the parallel arrangement of the channels.

Figure 19A:
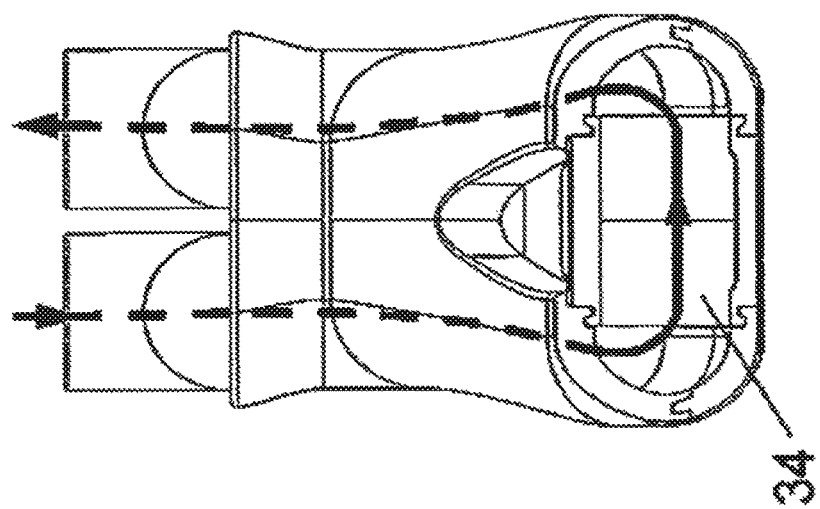
FIG. 19a is another view of the course of the flow of the air used for respiration through the adapter from FIGS. 16 and 17.
Figure 19B:
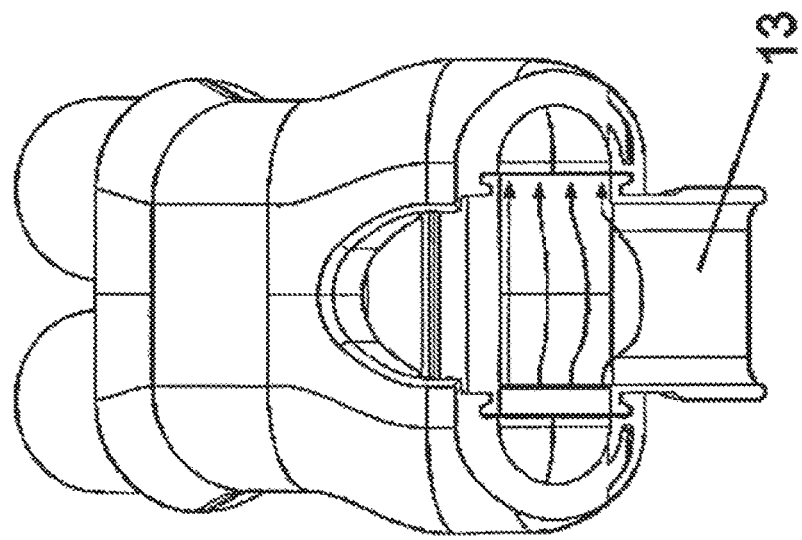
FIG. 19b is another view of the course of the flow of the air used for respiration through the adapter from FIGS. 16 and 17.

FIGS. 19a and 19b show the course of the air flow in the interior of the tube element 34. It can be seen especially in FIG. 19a that the dead space, which is defined theoretically by the inner volume of the connection nozzle 13, is reduced even further in practice by the partial inflow of fresh inhalation air into the nozzle and the flush-out effect achieved thereby. FIG. 19b clearly shows once again the flow path from the inspiratory channel of the adapter, through the tube element 34 and back through the expiratory channel The solution proposed in the introduction to the description and explained in detail in the description of the figures offers advantages over the hitherto known solutions in terms of handling by health care staff. Health care staff can adapt the curvature of the proximal tubes to the size of the child's head before the nasal adapter system according to the present invention is attached to the head. However, unlike in the prior-art solutions, a fine adaptation can be performed thereafter with the adapter already in place. As a result, it is possible to prevent to a great extent that nasal adapters not adapted optimally, to which masks or prongs are attached, from exerting stresses on the contact surface in question and from possibly leading as a consequence to irreparable damage to the nose or face. Optimal adaptation to the individual geometry of the child's head is guaranteed only by the combination of coarse adaptation and fine adaptation.

The rotatable coupling means between the proximal and distal breathing tubes offer the advantage over the prior-art connections by means of rigid conical plug-type connection that axial rotations of the distal tubes can be uncoupled from the proximal tubes. Rotation of the distal tubes does not therefore brings about any torque or a markedly reduced torque on the adapter and hence on the child's head than in case of a connection by frictional engagement.

As was described above, the cross-sectional area of the tubes can be increased and the flow resistance can thus be reduced in case of the use of the non-invasive tube cross sections proposed with unchanged width of the pair of tubes.

While specific embodiments of the invention have been shown and described in detail to illustrate the application of the principles of the invention, it will be understood that the invention may be embodied otherwise without departing from such principles.

The invention claimed is:

1. A nasal adapter system for use in non-invasive respiratory support, the system comprising:
a nasal adapter, which has a proximal end and a distal end, wherein the proximal end is designed for coupling to the nose of a patient to be respirated, and the distal end is designed for coupling with a respirator, the nasal adapter comprising:
an inspiratory channel;
an expiratory channel, the inspiratory channel and the expiratory channel extending between the proximal end and the distal end of the nasal adapter, the inspiratory channel and the expiratory channel each extending in parallel, and extend adjacent, to each other, the inspiratory channel and the expiratory channel being attached to each other through a common partition which separates breathing gas in the inspiratory channel and the expiratory channel from one another; a tube element held rotatably between the proximal ends of the channels, the tube element being provided with a through opening in an outer circumferential surface of the tube element; and
a connection nozzle, which is formed on an outer side of the tube element in alignment with the through opening, wherein the connection nozzle is designed for coupling with the nose of the patient to be respirated.

2. A nasal adapter system in accordance with claim 1, further comprising: proximal breathing tubes connected at the distal end of the nasal adapter, the first and second proximal breathing tubes each having an axial direction extending in parallel to each other, the first and second proximal breathing tubes being attached to each other through the circumferential surfaces of each of the first and second proximal breathing tubes.

3. A nasal adapter system in accordance with claim 2, further comprising a plastically deformable fiber, wherein the proximal breathing tubes are connected to one another and are coupled to the plastically deformable fiber with an attachment that extends in the axial direction of the tubes, wherein the deformable fiber comprises a metal wire with a circular or rectangular cross section, the plastically deformable fiber holding the proximal breathing tubes in a plurality of selectable positions.

4. A nasal adapter system in accordance with claim 2, further comprising:
a barrel joint; and
distal breathing tubes wherein the proximal breathing tubes and the corresponding distal breathing tubes are connected each by the barrel joint, so that each of the proximal breathing tubes is rotatable relative to the corresponding distal breathing tube.

5. A nasal adapter system in accordance with claim 1, wherein the tube element is held between the proximal ends of the channels such as to bring about a fluid connection between the proximal ends of the inspiratory channel and the expiratory channel.

6. A nasal adapter system in accordance with claim 1, wherein the distal ends of the inspiratory channel and of the expiratory channel are provided each with a connection adapter for connecting a proximal inspiratory tube and a proximal expiratory tube, respectively.

7. A nasal adapter system in accordance with claim 1, wherein the proximal ends of the inspiratory channel and of the expiratory channel are bent inwardly at an angle of about 90° each such that proximal openings of the channels face each other.

8. A nasal adapter system in accordance with claim 1, wherein the adapter has essentially an upper housing shell and a lower housing shell, which are connected to one another by bonding, welding or by locking means.

9. A nasal adapter system in accordance with claim 8, wherein:
the distal ends of the inspiratory channel and of the expiratory channel are provided each with a connection adapter for connecting a proximal inspiratory tube and a proximal expiratory tube, respectively; and
the inspiratory channel, the expiratory channel and the connection adapters are formed by the upper and lower housing shells.

10. A nasal adapter system in accordance with claim 8, wherein:
the two extensions are formed each on a proximal side of the lower and upper housing shells;
a 90° bend of the inspiratory channel is formed in one extension; and
a 90° bend of the expiratory channel is formed in the other extension.

11. A nasal adapter system in accordance with claim 1, wherein two extensions, between which the tube element is held, are formed at the proximal end of the adapter.

12. A nasal adapter system in accordance with claim 11, wherein the extensions have an end area with flat inner surfaces which face each other, the rotatable tube element is held in connection with the proximal openings of the channels and between the flat inner surfaces.

13. A nasal adapter system in accordance with claim 11, wherein the proximal end areas of the inspiratory channel and of the expiratory channel extend each in the form of a quarter toroid within the corresponding extensions.

14. A nasal adapter system in accordance with claim 1, wherein the connection nozzle is in connection with the interior space of the tube element and the two axial end openings of the tube element are in connection with the corresponding proximal openings of the inspiratory channel and the expiratory channel, respectively.

15. A nasal adapter system in accordance with claim 1, wherein a projection, which strikes a stop on the adapter housing in one end position, as a result of which the tube element is prevented from rotating excessively, is provided on the tube element.

16. A nasal adapter system in accordance with claim 1, wherein the design for coupling the connection nozzle with the nose of the patient to be respirated comprises a coupling for a nasal mask or a prong.

17. A nasal adapter system in accordance with claim 1, wherein the proximal openings of the inspiratory channel and of the expiratory channel have a circular cross section, which coincides with the cross section of the cylindrical tube element.

18. A nasal adapter system in accordance with claim 1, wherein the tube element is held between the proximal openings of the inspiratory channel and of the expiratory channel such as to make possible a change in the angular position between the nasal adapter and the connection nozzle.

19. A nasal adapter system in accordance with claim 1, wherein:
nasal adapter has a first shell and a second shell connected to each other, the first and second shells each defining a portion of the inspiratory channel and the expiratory channel, the partition being formed by one of the first shell, the second shell, and/or a combination of the first and second shells.

20. A nasal adapter system comprising:
a nasal adapter, which has a proximal end and a distal end, wherein the proximal end is designed for coupling to the nose of a patient to be respirated, and the distal end is designed for coupling with a respirator, the nasal adapter comprising:
an inspiratory channel with an inspiratory channel distal end and an inspiratory channel proximal end having an inspiratory channel opening;
an expiratory channel with an expiratory channel distal end and an expiratory channel proximal end having an expiratory channel proximal end opening;
a tube element rotatably connected to the inspiratory channel at or adjacent to the inspiratory channel proximal end and rotatably connected to the expiratory channel at or adjacent to the expiratory channel proximal end, the tube element having a tube element flow passage in fluid communication with the inspiratory channel via the inspiratory channel opening and in fluid communication with the expiratory channel via the expiratory channel proximal end opening, the tube element having an outer circumferential surface with a through opening; and
a connection nozzle extending from the outer circumferential surface of the tube element, the connection nozzle having a nozzle flow passage in fluid communication with the tube element flow passage via the through opening, wherein:
the inspiratory channel and expiratory channel, at the distal end of the nasal adapter, respectively define a breathing tube connection interface, each breathing tube connection interface being for connection of a separate breathing tube;
the connection nozzle defines a connection interface for connection of a nasal mask or a prong;
the inspiratory channel receiving breathing gas from the inspiratory channel distal end and flowing all of the breathing gas to the tube element;
the expiratory channel receiving exhaled gas from the tube element and flowing all of the exhaled gas to the expiratory channel distal end.

21. A nasal adapter system in accordance with claim 20, wherein:
the proximal ends of the inspiratory channel and the expiratory channel define a ball socket;
the tube element has a spherical element arranged in the ball socket.

22. A nasal adapter system in accordance with claim 21, wherein:
the spherical segment is rotatable and pivotable in the ball socket in all directions.

23. A nasal adapter system comprising:
a respiration device having an inspiratory tube and an expiratory tube;
a nasal adapter, which has a proximal end and a distal end, wherein the proximal end is designed for coupling to the nose of a patient to be respirated, and the distal end is designed for coupling with the respiration device, the nasal adapter comprising:
an inspiratory channel with an inspiratory channel distal end connected to, and receiving breathing gas from, said inspiratory tube, said inspiratory channel having an inspiratory channel proximal end having an inspiratory channel opening;

an expiratory channel with an expiratory channel distal end connected to, and flowing exhaled gas to, said expiratory tube, said expiratory channel having an expiratory channel proximal end having an expiratory channel proximal end opening;

a tube element rotatably connected to said inspiratory channel proximal end and rotatably connected to said expiratory channel proximal end, said tube element having a tube element flow passage in fluid communication with said inspiratory channel via said inspiratory channel opening and in fluid communication with said expiratory channel via said expiratory channel proximal end opening, said tube element having an outer circumferential surface with a through opening; and a connection nozzle extending from said outer circumferential surface of said tube element, said connection nozzle having a nozzle flow passage in fluid communication with said tube element flow passage via said through opening.

\* \* \* \* \*